United States Patent
Morris et al.

(10) Patent No.: US 10,288,588 B2
(45) Date of Patent: May 14, 2019

(54) PREDICTION OF FUEL PROPERTIES

(71) Applicants: Robert E. Morris, Silver Spring, MD (US); Mark H. Hammond, Alexandria, VA (US); Kevin J. Johnson, Alexandria, VA (US); Jeffrey A. Cramer, Alexandria, VA (US)

(72) Inventors: Robert E. Morris, Silver Spring, MD (US); Mark H. Hammond, Alexandria, VA (US); Kevin J. Johnson, Alexandria, VA (US); Jeffrey A. Cramer, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 305 days.

(21) Appl. No.: 14/869,944

(22) Filed: Sep. 29, 2015

(65) Prior Publication Data

US 2016/0091467 A1 Mar. 31, 2016
US 2016/0209379 A9 Jul. 21, 2016

Related U.S. Application Data

(60) Provisional application No. 62/056,666, filed on Sep. 29, 2014, provisional application No. 62/030,360, filed on Jul. 29, 2014.

(51) Int. Cl.
*G01N 30/72* (2006.01)
*G01N 30/86* (2006.01)
*G01N 33/28* (2006.01)

(52) U.S. Cl.
CPC ..... *G01N 30/7206* (2013.01); *G01N 30/8675* (2013.01); *G01N 33/2829* (2013.01)

(58) Field of Classification Search
CPC .......... G01N 30/7206; G01N 30/8675; G01N 33/2829
See application file for complete search history.

(56) References Cited

U.S. PATENT DOCUMENTS 4,835,708 A * 5/1989 Frans ............... G01N 30/8675
702/27
5,699,269 A * 12/1997 Ashe ............... G01N 33/2823
436/29

(Continued)

*Primary Examiner* — Justin Seo
*Assistant Examiner* — John M Royston
(74) *Attorney, Agent, or Firm* — US Naval Research Laboratory; William P. Ladd

(57) ABSTRACT

A system is described that includes a known fuels database of data from gas chromatography-mass spectrometry analyses of a library of fuels with known fuel properties for a multiple known fuel samples. Gas chromatography-mass spectrometry equipment can acquire gas chromatography-mass spectrometry data for an unknown fuel sample. A metaspectrum module can accept and transform the gas chromatography-mass spectrometry data collected by the gas chromatography-mass spectrometry equipment for the unknown fuel sample into a single metaspectrum for the unknown fuel sample, wherein the metaspectrum is a quantitative representation of every compound detected in the unknown fuel sample. A correlation module can correlate the metaspectrum for the unknown fuel sample to a plurality of fuel properties of known fuel samples using a regression model to predict fuel properties for the unknown fuel sample. A reporting module can report the fuel properties for the unknown fuel sample to a user.

20 Claims, 6 Drawing Sheets

(56) References Cited

U.S. PATENT DOCUMENTS

| | | | |
|---|---|---|---|
| 2006/0125826 A1* | 6/2006 | Lubkowitz | G01N 30/8675 345/440 |
| 2008/0271885 A1* | 11/2008 | Kaminsky | E21B 36/04 166/245 |
| 2008/0296487 A1* | 12/2008 | Lubkowitz | G01N 30/78 250/283 |
| 2009/0282897 A1* | 11/2009 | Bertoncini | G01N 30/463 73/23.38 |
| 2010/0211329 A1* | 8/2010 | Farquharson | G01N 21/359 702/28 |
| 2013/0080073 A1* | 3/2013 | de Corral | G01N 30/86 702/23 |
| 2014/0229010 A1* | 8/2014 | Farquharson | G01N 33/22 700/272 |

* cited by examiner

PREDICTION OF FUEL PROPERTIES

CROSS-REFERENCE TO RELATED APPLICATIONS

This application claims priority to provisional patent application entitled, "Software tool to provide compositional information and predicted properties of mobility fuels from chemometric modeling of gas chromatography-mass spectrometry (GC-MS) data," filed on Jul. 29, 2014, and assigned U.S. Application No. 62/030,360, and "Software tool to provide compositional information and predicted properties of mobility fuels from chemometric modeling of gas chromatography-mass spectrometry (GC-MS) data," filed on Sep. 29, 2014, and assigned U.S. Application No. 62/056,666; the entire contents of both which are hereby incorporated by reference.

FIELD OF THE INVENTION

The present disclosure relates to a tool for determining compositional information and predicted properties of mobility fuels.

BACKGROUND

Research has been ongoing to determine ways to reduce the time, manpower, and amounts of fuel required to measure standard ASTM specification properties. These properties are not only useful for on-site fuel diagnostics, but are also vital to overall fuel certification procedures. The end goal has typically been envisioned as a stand-alone tool capable of predicting multiple fuel performance properties using only a single small fuel sample subjected to a single analytical technique. Previous research efforts have typically focused upon analytical techniques that do not provide direct information regarding chemical composition, such as near-infrared (NIR) spectroscopic data. These efforts were successful, resulting in the development of a stand-alone prototype instrument, which predicted various critical specification fuel properties using the partial least squares (PLS) modeling of NIR spectroscopic data. The instrument was primarily trained on and applied to standard petrochemical fuels, but was also adapted to accommodate the accurate analysis of Fischer-Tropsch (FT) synthetic fuels, fuels derived from biomass, and blends of these two fuel types with petrochemical fuels, as well as the accurate identification of ultra-low sulfur diesel (ULSD) fuels.

Other research is also generally focused on development of predicative models based on spectroscopic, and especially NIR, data. This focus exists for many reasons, including the relative ease with which such data can be collected and accommodated for chemometric model development and subsequent stand-alone tool development. However, research has shown that adapting NIR property prediction models based on petrochemical fuels to properly accommodate non-petrochemical fuels generally requires a devoted research effort. In a best-case scenario, models must be adapted to each possible alternative fuel type; while in a worst-case scenario, models must be redeveloped for each individual fuel within a type. Critically, there is an inherent unpredictability in both the type and quantity of non-petrochemical fuels that might exist in worldwide fuel populations for the near future. Therefore, it was determined that the accommodation of non-petrochemical fuels could not be realistically performed on a case-by-case basis. Although some strategies have been developed to improve NIR fuel property modeling algorithms in an automated fashion to enhance the performance of the previously developed stand-alone prototype instrument, these were discrete, incremental modeling improvements that are insufficient to address the fundamental challenge presented by uncalibrated fuel types.

Accordingly, there remains a need in the art for a new analysis strategy based on a more granular, chemical-by-chemical assessment of fuel composition than is possible with spectroscopic methods, such as NIR, to accommodate the unpredictable nature of future fuels. This strategy would concurrently address a long-standing concern of practical fuel implementation, true fit-for-purpose (FFP) fuel modeling based on fuel composition. A great deal of information regarding fuel composition, and even fuel performance, can already be obtained from GC-MS data, which makes it an ideal analytical technique upon which to base the in-depth and universally-applicable fuel analysis strategy required for the desired software tool.

SUMMARY OF THE INVENTION

According to one aspect of the invention, a method is described that includes the steps of acquiring a plurality of data from gas chromatography-mass spectrometry analyses of a library of fuels with known fuel properties for a plurality of known fuel samples. Next, gas chromatography-mass spectrometry data can be acquired from an unknown fuel sample. The gas chromatography-mass spectrometry data from the unknown fuel sample can be transformed into a single metaspectrum for the unknown fuel sample with a metaspectrum module, wherein the metaspectrum is a quantitative representation of every compound detected in the unknown fuel sample and the metaspectrum module is implemented in a computer system that comprises instructions stored in a machine-readable medium and a processor that executes the instructions. Finally, the metaspectrum for the unknown fuel sample can be correlated to a plurality of fuel properties of known fuel samples using a regression model to predict fuel properties for the unknown fuel sample with a correlation module, wherein the correlation module is implemented in a computer system that comprises instructions stored in a machine-readable medium and a processor that executes the instructions.

According to another aspect of the invention, an system is described that includes a known fuels database which includes data from gas chromatography-mass spectrometry analyses of a library of fuels with known fuel properties for a plurality of known fuel samples. Gas chromatography-mass spectrometry equipment can be configured to acquire gas chromatography-mass spectrometry data for an unknown fuel sample. A metaspectrum module can be configured to accept and transform the gas chromatography-mass spectrometry data collected by the gas chromatography-mass spectrometry equipment for the unknown fuel sample into a single metaspectrum for the unknown fuel sample, wherein the metaspectrum is a quantitative representation of every compound detected in the unknown fuel sample. A correlation module can be configured for correlating the metaspectrum for the unknown fuel sample to a plurality of fuel properties of known fuel samples using a regression model to predict fuel properties for the unknown fuel sample. Finally, a reporting module can be configured to report the fuel properties for the unknown fuel sample to a user.

These and other aspects, objects, and features of the present invention will become apparent from the following detailed description of the exemplary embodiments, read in conjunction with, and reference to, the accompanying drawings.

BRIEF DESCRIPTION OF THE DRAWINGS

The following description and drawings set forth certain illustrative implementations of the disclosure in detail, which are indicative of several exemplary ways in which the various principles of the disclosure may be carried out. The illustrated examples, however, are not exhaustive of the many possible embodiments of the disclosure. Other objects, advantages and novel features of the disclosure will be set forth in the following detailed description of the disclosure when considered in conjunction with the drawings, in which.

DETAILED DESCRIPTION OF EXEMPLARY EMBODIMENTS

Figure 1:
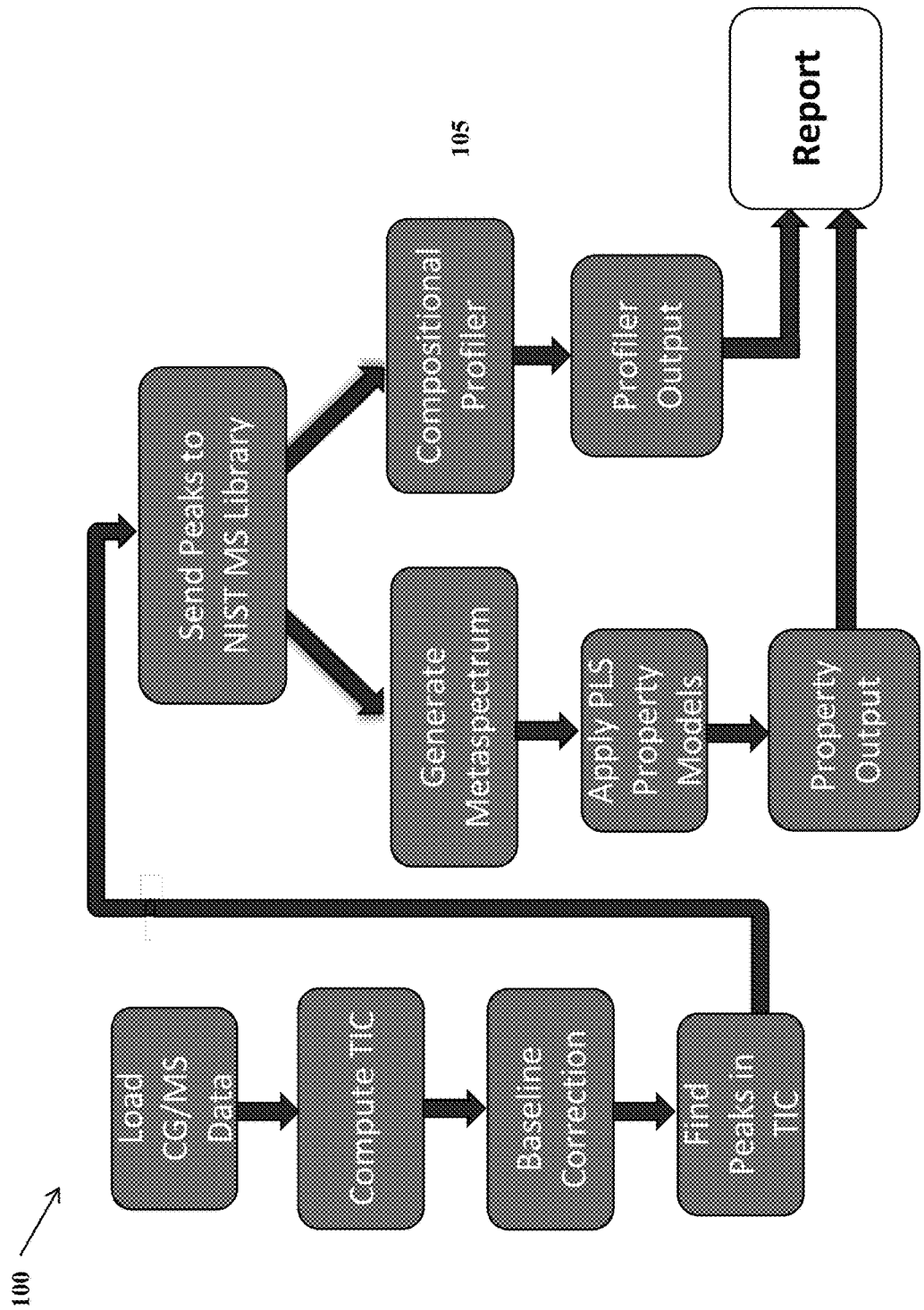
FIG. 1 is a flow chart depicting computational steps of a software tool, in accordance with an exemplary embodiment of the invention.

One or more embodiments or implementations are hereinafter described in conjunction with the drawings, where like reference numerals refer to like elements throughout, and where the various features are not necessarily drawn to scale.

FIG. 1 is a flow chart 100 depicting steps of a software tool in accordance with an exemplary embodiment of the invention. Specifically, FIG. 1 depicts the computational steps performed in the software tool for predicting properties of fuels from chemometric modeling of gas chromatography-mass spectrometry (GC-MS) data. Fuel property predictions can be implemented by first acquiring data from GC-MS analyses of a library of fuels with known properties, a known fuels database. These data can be subsequently transformed into chemical compound-indexed "metaspectra," which can then be related to their known fuel properties via multiple multivariate regression models. These regression models can then be incorporated into a standalone software tool that enables an end user to load GC-MS data from new (i.e. non-library) fuels, calculate the corresponding metaspectral data, and apply it to the regression models in order to calculate a list of predicted fuel property values.

For the GC-MS data acquisition, GC-MS data can initially be collected from a library of unique jet and diesel fuel samples. There can be thousands of samples in the library, and information can be stored in a database. These fuel samples, stored in the database, can include corresponding fuel performance properties as measured using standard ASTM methodologies. These data serve as "training" data, i.e. the data used to construct the fuel property prediction models. In accordance with an exemplary embodiment of the invention, the following GC-MS instrument parameters can be considered optimal for invention's contemporary operation: (1) Instrument: Agilent 7890A GC connected to an Agilent 5975C MSD with a heated transfer capillary line (250° C.); (2) Column: 60 m×0.25 mm×0.5 µm Agilent DB-1 ms fused silica with a helium flow of 2.0 mL/min; (3) MS Parameters: Source temperature 250° C., Quad temperature 150° C., Scan Mode scanning from 35-400 m/z with a threshold of 250 and a gain factor of 1.5 (4) Oven Program: 40° C. for 2 min, 5° C./min to 165° C., 2.5° C./min to 265° C., 10° C./min to 295° C. for 0 min, Total Run Time of 70 min; (5) GC Inlet: Split mode, 35:1 split ratio, 285° C.; (6) Sample Preparation: dilute 5:1 with methylene chloride; and (7) Injection Volume: 0.5 µL. One of ordinary skill in the art would understand that alternatives to these parameters include differences in how the initial training GC-MS data and data from unknown fuels are collected and modeled, as well as differences in how the software itself could be operated.

Figure 3:
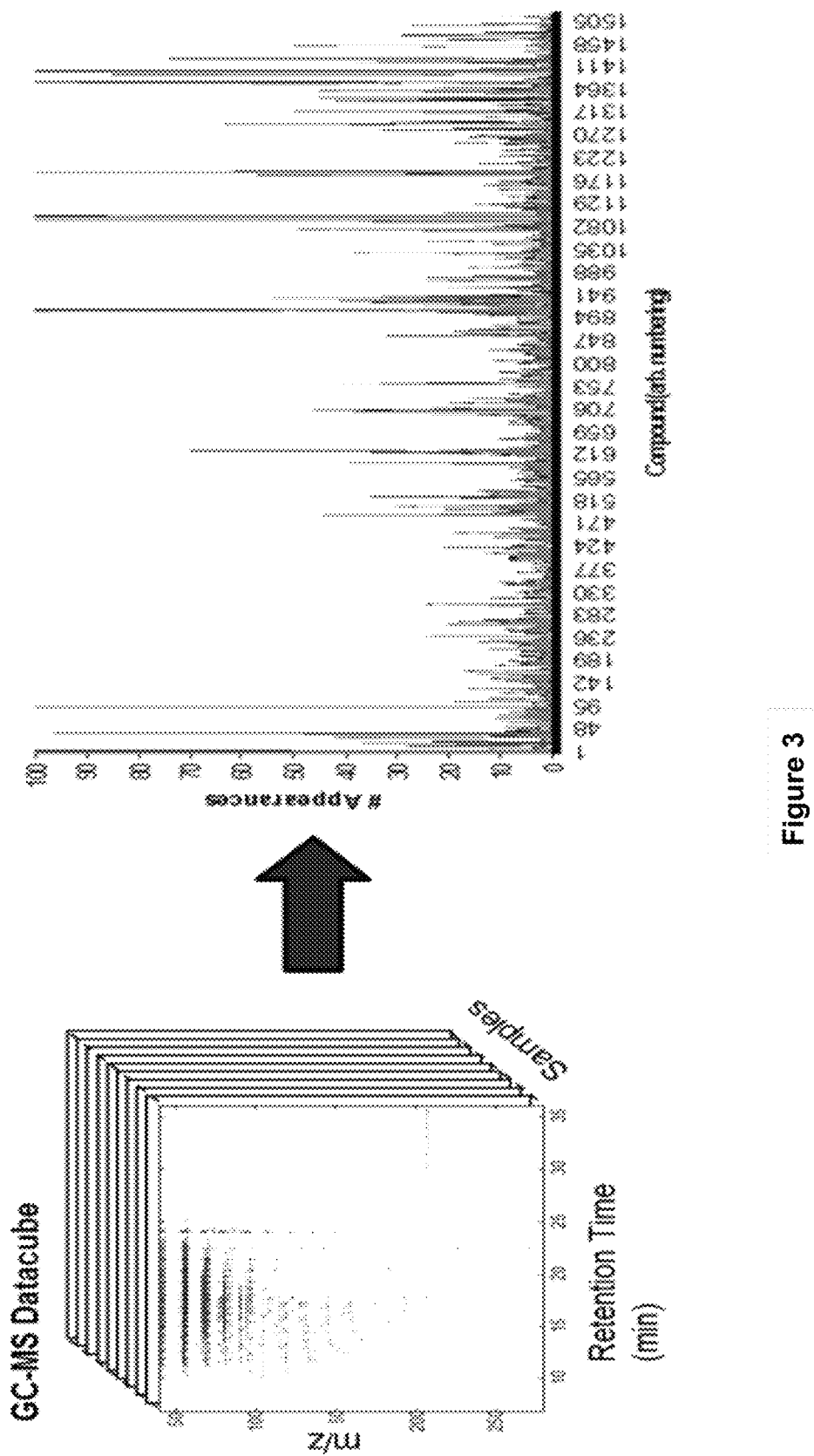
FIG. 3 represents metaspectra data abstraction, in accordance with an exemplary embodiment of the invention.

Once collected, the GC-MS data from each sample can then be transformed, with a metaspectrum module from a three-dimensional data set (i.e. instrument response×mass/charge ratio×retention time) into a two-dimensional data set, yielding a single "metaspectrum" (abundance×compound identity) for each fuel. FIG. 3 represents a metaspectral data abstraction, in accordance with an exemplary embodiment of the invention. Specifically, FIG. 3 depicts an overlay of fuel metaspectra, showing compound abundances, indexed by an arbitrary compound identification number. The "metaspectrum" is a one-dimensional abstraction that is a quantitative representation of every compound detected in the fuel sample. Each element in the array is assigned to one of the discrete compounds found in a fuel library, and the value of each element can be related to the abundance of that compound. Reduced dimensionality allows chemometric modeling to be performed on the second order GC-MS data set. These data are subsequently used for multivariate regression modeling of fuel properties.

Metaspectra can be calculated by first locating all discernible chromatographic peaks in a GC-MS data set. Each peak can then be identified against a mass spectral database (for example, the NIST mass spectral database), and the area of that peak can be tabulated as the abundance of the matched compound in the fuel sample corresponding to the GC-MS data set. A peak area threshold value can be used to estimate match quality, and matches found for peaks below this threshold can be disregarded for the purposes of inclusion in the metaspectrum. In the event that a chromatographic peak is not matched with any of the fuel-related indexed compounds, the second best match can be considered, on the principle that, although the match may not strictly identify the peak, the underlying compound is likely to be structurally similar, and thus contribute to fuel properties in a similar fashion. Each metaspectrum thus represents the compositional information obtained using GC-MS as a compound-indexed list of GC-MS signal abundances.

Next, calculated metaspectra of library fuels can be correlated with a correlation module to fuel properties using partial least squares (PLS) regression in essentially the same manner as one would with conventional spectra, such as those obtained with NIR spectrophotometry. This process can be an iterative, multi-step strategy that was developed based on an earlier version of the analysis that did not include peak area information. However, when the metaspectral data constructions were updated with peak information, the iterative strategy was disregarded in favor of a straightforward application of uninformative variable elimination PLS (UVE-PLS). While the use of UVE-PLS adds the ability to remove uninformative portions of the metaspectra from overall modeling results, the procedure functions in much the same way as other PLS modeling procedures. To avoid model overfitting, the number of latent variables (#LV) for individual models can be determined using an F-test applied to the results of a full data cross-validation. It should, however, be noted that a final PLS model can be constructed from the compounds remaining after the application of UVE-PLS. This final PLS model, in turn, produces less optimistic error measures than would be obtained using cross-validated UVE-PLS directly, and, thus, these PLS-based errors are more suitable for predicting how a model will perform with uncalibrated data.

The fuel properties of new, non-library (i.e., uncalibrated) fuel samples can then be predicted by the final PLS models constructed during the training process. This functionality can be implemented within a software tool that can be designed to perform all required preprocessing and processing steps automatically to provide fuel property predictions, as well as other fuel-related GC-MS analytics related to fuel composition elucidation, as a stand-alone user-friendly software package.

All calculations can occur without directly consulting an operator, who simply loads the GC-MS data collected from a fuel sample with gas chromatography-mass spectrometry equipment collected outside of the software tool. These data are then reinterpreted as a metaspectrum with the metaspectrum module, which can then be applied to the previously produced, in-program PLS fuel property prediction models and correlated with the correlation module. These fuel property predictions can, finally, be presented to the operator as a straightforward list of predicted fuel property values with a reporting module.

Figure 4:
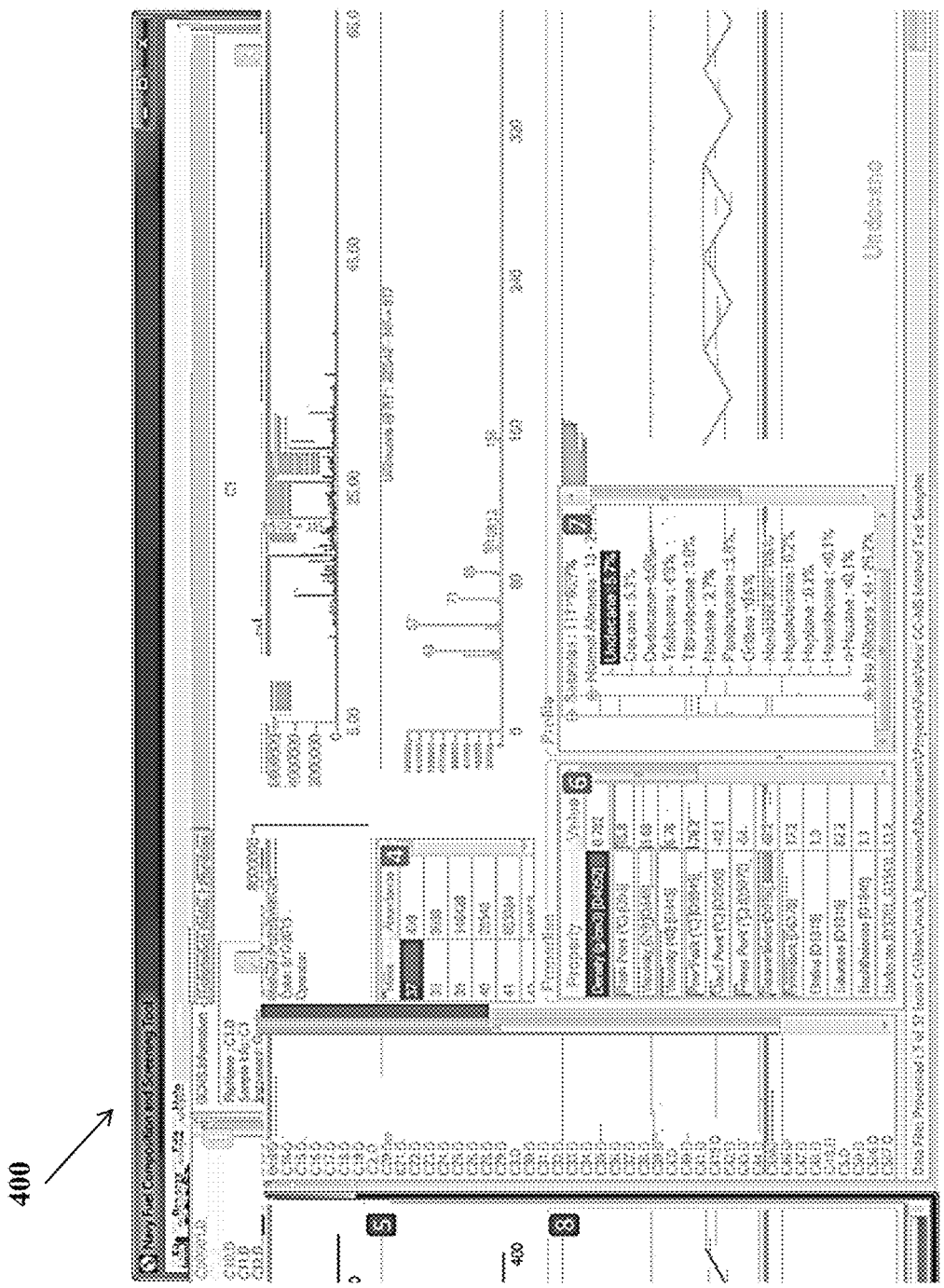
FIG. 4 is a depiction of a software tool's user interface, in accordance with an exemplary embodiment of the invention.

FIG. 4 is a depiction of a software tool's user interface, in accordance with an exemplary embodiment of the invention. In an exemplary embodiment of the invention, the user interface can include the following display data: (1) List of data files, (2) GC-MS data file properties, (3) Total Ion Chromatogram (TIC) of selected file, showing selected retention time of a selected component, (4) m/z table for selected component, (5) m/z plot for selected component, (6) PLS-predicted Properties, (7) Hydrocarbon compositional profile, and (8) Chemical structure of selected compound in Hydrocarbon Profile. Other information can also be displayed. In addition to the graphic output, property predictions and compositional profiler results can also be saved to a local hard drive in binary data files, in the event that end users would like to export the data for their own records or data analysis procedures.

The software tool can be folded into a standalone Windows executable package that performs other fuel-characterization functions. However, one of ordinary skill in the art would understand the software tool could be ported to other platforms as a separate utility, or be incorporated into different, larger-scoped software packages. Furthermore, the user interface can continuously be adjusted to more ably facilitate user-friendliness. These adjustments typically do not require changes to the modeling itself or the fundamental results being reported by the software.

In summary, the exemplary embodiment of the invention is unique among similar efforts, including NFPM and GC-MS analysis strategies, because of the scope of the software tool's intended purpose. At least thirty fuel properties can be predicted at present, but the tool can easily be expanded to incorporate additional fuel properties, or new fit-for-purpose categorizations through additional GC-MS data modeling, as understood by one of ordinary skill in the art.

Figure 2:
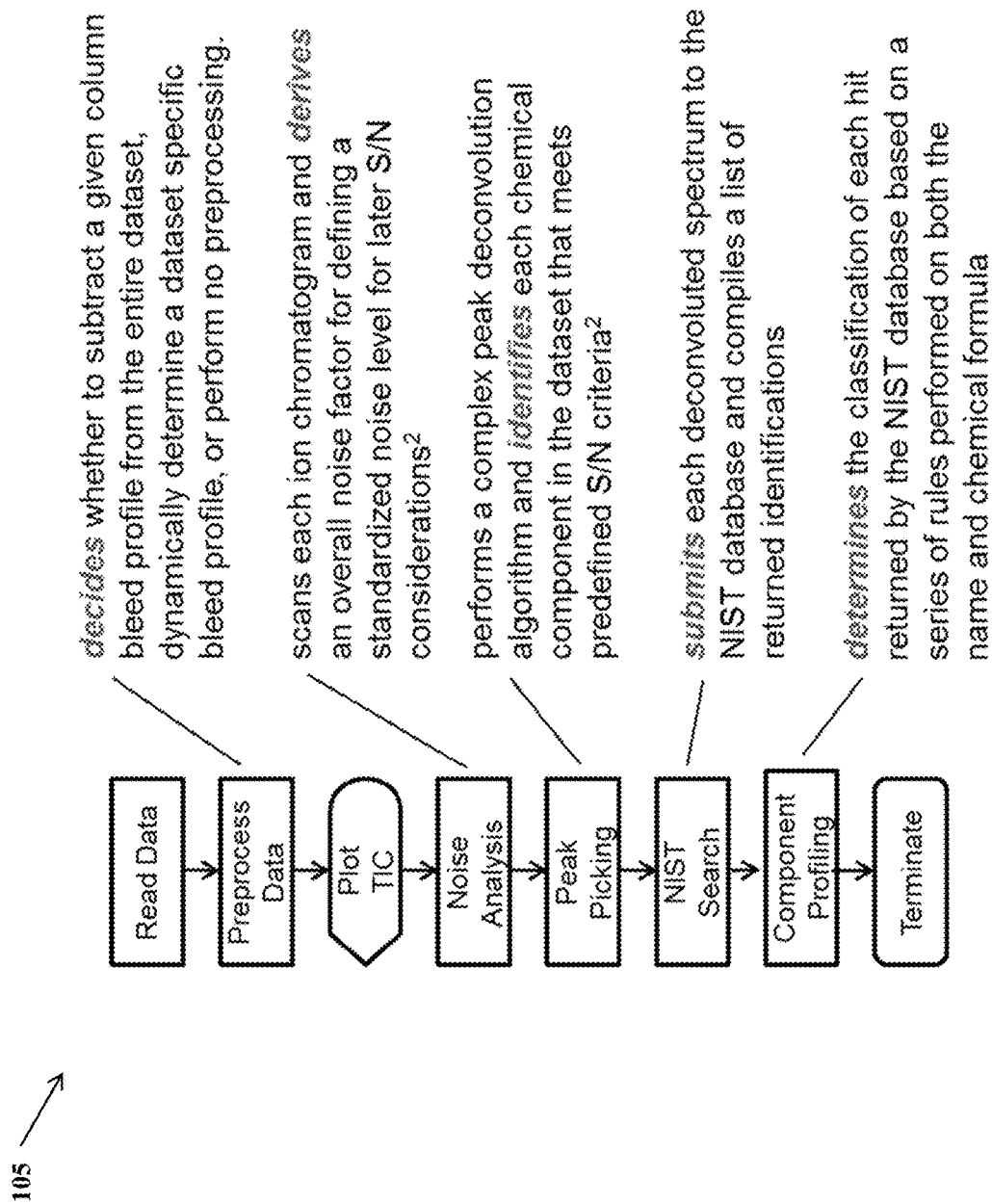
FIG. 2 is a flow chart depicting steps of a compositional profiler of the software tool, in accordance with an exemplary embodiment of the invention.

The fuel properties can also be modeled in a novel manner that provides an enhanced capacity to accommodate future fuels, regardless of composition, because compositional information is correlated to fuel properties directly. FIG. 2 is a flow chart depicting steps of a compositional profiler 105 of the software tool, in accordance with an exemplary embodiment of the invention. Because every compound in a sample can potentially inform every fuel property prediction during the model construction process, this software has an inherent advantage over other, only indirectly compositional techniques, and the software's modeling results in more accurate and robust fuel property prediction results. This capacity is critically important in the context of fit-for-purpose fuel modeling in the context of both petrochemical and alternative fuels, as knowing what purpose a fuel is fit for does not necessarily require discrete fuel property quantifications, but rather a distinct type of performance untethered to assumptions of fuel composition.

Current fuel property prediction models are based on those fuels currently available. While this amounts to well over a thousand fuels at present, additional fuels, especially those representing alternative fuels and other under-represented and non-represented fuel types, would be expected to make overall fuel property predictions more accurate, or at least more robust, i.e. more capable of accurately predicting the fuel properties of uncalibrated fuels and/or fuel types. Therefore, the exact composition of the training data is expected to increase sporadically as additional fuels are incorporated into updated model constructions.

Although GC-MS data are used for the current analysis procedure, in accordance with an exemplary embodiment of the invention, there is every reason to believe that data produced using an expanded version of GC-MS could provide even better property prediction results. Specifically, Gas Chromatography×Gas Chromatography–Time-of-Flight Mass Spectrometry (GC×GC–TOFMS) could also be used to model fuel properties using existing modeling procedures. Because the current method of data modeling requires the translation of mass spectra into distinct compound identifications, there is nothing that would prevent a similar identification procedure for the mass spectra present in GC×GC–TOFMS data. It has yet to be determined if this substantial increase in raw data and, hence, data collection and subsequent calculation times will yield commensurately more accurate and precise fuel property models.

Furthermore, GC-MS data do not necessarily need to be collected under the exact instrument parameters described previously. Alternative instrument settings can periodically be evaluated to determine if they will enhance property model performance. In addition, sampling parameters, such as the amount of sample dilution, are similarly evaluated in the context of enhancing the overall analysis strategy.

Data models can be created outside of the actual software tool and imported into the tool when they are completed. Because the multi-step model construction procedure can be performed in the software itself, it can be possible to incorporate an ad hoc model construction procedure for fuel properties not included in the original model construction process. Such a course of action, however, would give users the ability to construct models for themselves. Of course, one of ordinary skill in the art would understand that with no effective quality control on user created models, it could lead to poor property predictions. Therefore, any in-software model construction capabilities would necessarily be kept separate from the models included in the software itself, so that the pre-existing models would not be affected by potentially damaging model augmentations.

The modeling procedure requires that mass spectra be first interpreted as compound-oriented metaspectra, using a mass spectral database search, prior to fuel property prediction. However, in an alternative embodiment, a smaller, customized database can more directly model those compounds that are most likely to appear in mobility fuels. This database could minimize the most problematic of possible compound misidentifications, as the available compound identification possibilities themselves would no longer allow for them. However, one of the primary reasons that GC-MS data are being modeled in the first place is to allow for any and all possible compounds to influence property predictions as necessary. If a smaller database is used, then a capability will need to be included to allow uncalibrated compounds to maintain some level of influence over predictions.

In one specific alternative embodiment, the estimation of uncalibrated compounds as chemically or spectrally similar calibrated compounds can be performed. This embodiment can be similar to the "second best match" concept found in the calculation of metaspectra. Additionally, allowing entire fuel component classes, such as "aromatics" and "phenols", to influence predictions in a collective fashion could allow compounds that belong to these categories a commensurate influence regardless of whether or not they would influence fuel property predictions individually.

The accumulation of mass spectral identifications into metaspectra has only an indirect relationship to true compound quantification. The abundance of any given compound relies upon the total peak area, which is, in turn, dependent on compound-specific, mass-selective response factors. Another possibility for quantification, then, could arise from the determination of mass-selective response factors using mass-selective detectors, either in concert with the type of MS data already collected or in a separate data collection meant to augment unrelated MS data collections. This could be implemented either on a per-compound basis or per-compound class basis to make both fuel property predictions and compositional profiler results truly quantitative.

In a current embodiment of the invention, compound identifications can be disregarded if they are based on small peak areas values. Compound identifications can also potentially be disregarded if the match quality itself, as defined by a quantity known as a Match Factor (MF), is too low. Both of these parameters are occasionally re-investigated to determine if up-to-date modeling procedures can be enhanced by the data removals that some combination of these two parameters could provide. It is also, of course, possible that alternative "cutoff" parameters can be used to fine-tune metaspectral production methods in a similar fashion.

In addition to the possible modifications to the mass spectral database and how compound identifications can be more precisely quantified, it can also be possible to remove the database search from the modeling procedure entirely as the use of a database search may be introducing errors and analysis assumptions that need not be introduced. Accordingly, work is continuously being performed to directly model GC-MS data based directly on the raw data as it is originally collected, such as with a shape-based data modeling approach.

As noted previously, the multi-step data modeling strategy is no longer performed as part of the operation of the software tool as it includes an extensive data unmasking process that has not been necessary since the implementation of peak areas into the metaspectral data. However, it is possible that this multi-step strategy could be revisited in the future to improve modeling results. Any given step in the strategy, or the strategy in its entirety, could, in turn, potentially be modified to create more accurate modeling results, enhance the data unmasking, or even circumvent the data unmasking entirely. Any of these modifications might allow the software incorporating the results models to more fully serve its intended purposes.

One of ordinary skill in the art would understand that the though many fuel properties are currently modeled, many more fuel properties could theoretically be implemented into the software, which, again, is one of the overall, novel advantages of the software. Additional fuel properties would allow the software tool to function more ably in the context of FFP fuel property assessment.

The property predictions and compound profiling in the software tool are based on analysis of gas chromatography-mass spectrometry (GC-MS) data. Electron impact ionization mass spectrometry is not quantitatively linear with respect to analyte concentration due to differences in molecular ionization efficiencies of different classes of compounds. In addition, the mass analyzer electron capture detector response within a given class of compounds is also affected by the molecular weight, or number of carbons in an analyte molecule. Therefore, in order to report quantitative results in mass percent, response factor calibrations can be developed for different fuel compound classes, and a detector response calibration factor can be developed to correct for the differing detector responses to different types of analytes, in accordance with an exemplary embodiment of the invention.

Compound class response factors can be developed by simultaneous analysis of known mixtures consisting of mixtures of various compound classes contained in fuels by GC-MS and GC with flame ionization detection (GC-FID). FID response is linearly proportional to the mass of carbon in the sample. The MS and FID results can be correlated to develop the class average of the ratio of the response between the two types of instruments to correct for the MS response and convert to a mass percentage, similar to what an FID response would give.

This data can also be used to determine an additional correction to adjust the MS detector response as a function of the carbon number of the analyte molecules. These class-specific libraries of carbon number factors can be implemented in the software tool to provide quantitative results of compound abundances in mass percent, and to help ensure that the property predictions are quantitatively accurate.

Different lots or batches of fuels are commonly co-mingled in the fuel supply system and onboard vessels when tanks are topped off. Occasionally, when two in-specification fuels are mingled, the resultant blends can be found to be unstable, or can fail critical specification property requirements. This is commonly referred to as poor compatibility. In addition, alternative fuels are envisioned to be deployed as blends with their petroleum-derived fuel counterparts. A necessary facet of the alternative fuel certification process is to determine the optimal amount of a particular alternative fuel that can be blended with a typical petroleum fuel. This is currently performed in laboratories through a series of specification tests performed on a range of blending ratio samples.

In accordance with an exemplary embodiment of the invention, as a certification screening tool, the software tool can simulate the results of these laboratory tests by performing mass factor corrections, then mathematically blending GC-MS data, previously analyzed by the software tool, from two fuels with a blending module. By operating on the simulated fuel blends, the software tool can predict the specification properties and report the composition of the composite blend.

In the software tool, the user can select the two fuels to be blended, designated "A" and "B". The software tool can then operate on the compound abstraction vectors of the two chosen samples by normalizing the magnitudes of the two vectors, then applying the appropriate mass factors and detector corrections. The software tool can then mathematically combine the profiled compounds from each sample in increments of 10%, and calculate the properties at each blending increment step.

Figure 5:
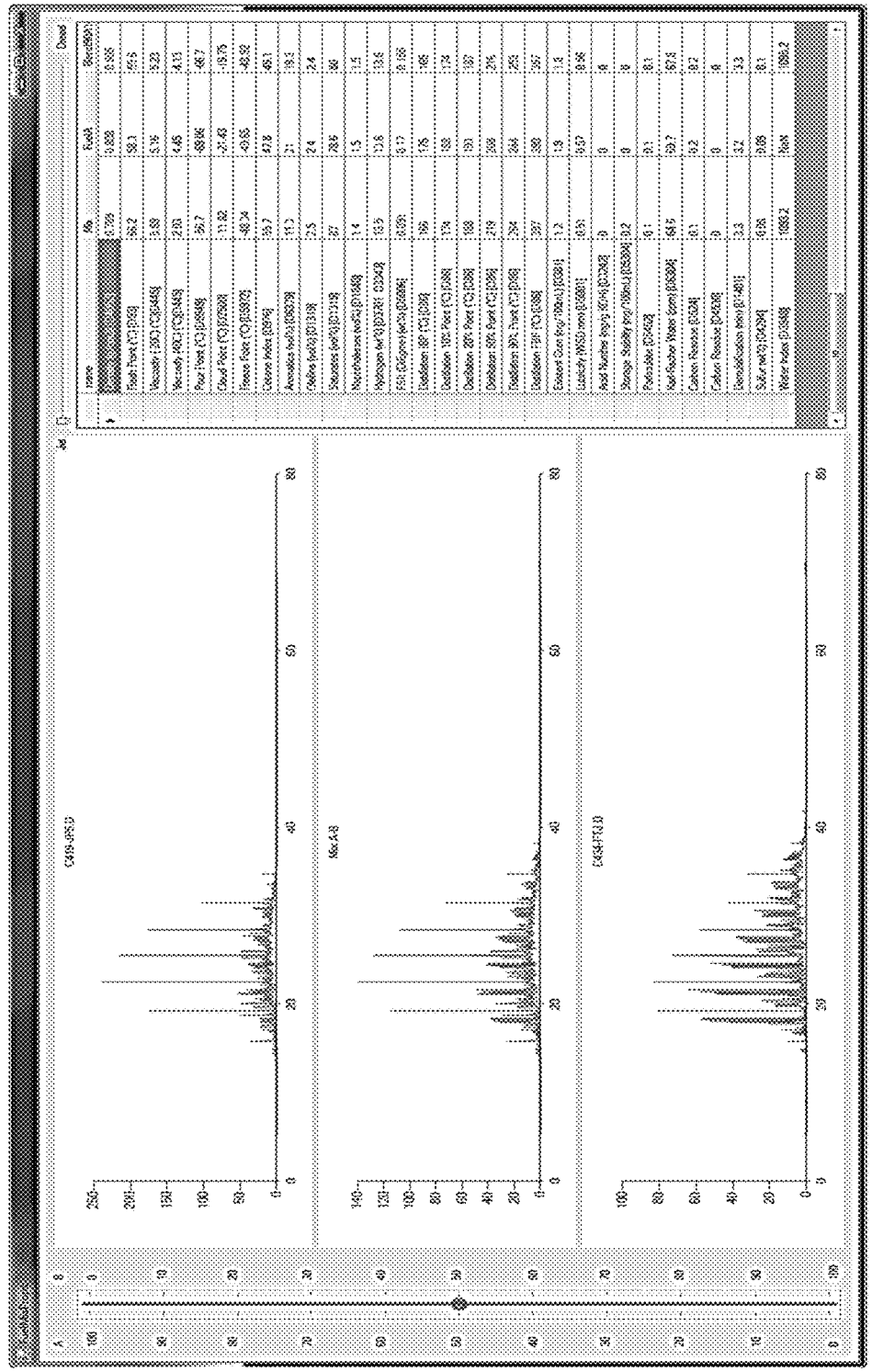
FIG. 5 is a simulated fuel blending display window, in accordance with an exemplary embodiment of the invention.

FIG. 5 is a simulated fuel blending display window 500, in accordance with an exemplary embodiment of the invention. The exemplary software tool display, shown in FIG. 5, represents the TIC of the two selected fuels on the top and bottom graph, along with the "blended" TIC based on the ratio of the slider on the left side. The predicted properties of each blend are shown in the table on the right side of the window, with the first column being a live display that changes, in accordance of the position of the slider on the left side of the window.

The software tool can include a blending function, in accordance with an exemplary embodiment of the invention, which is displayed in a separate window, such that the main software tool window can remain open and can be operated independently of the blending window. This can allow the operator to independently view other fuel samples to compare with the blended fuel results. The predicted properties and compositional profiles of the simulated blends can be saved in a Microsoft Excel spreadsheet format, or other similar spreadsheet as known to one of ordinary skill in the art. This capability can allow the software tool to be used to predict the specification compliance of binary blends of any two fuels. The computational methods used in the software tool's simulated blending algorithms can be designed such that they can be extended to predict the properties of blends consisting of any number of fuels.

Figure 6:
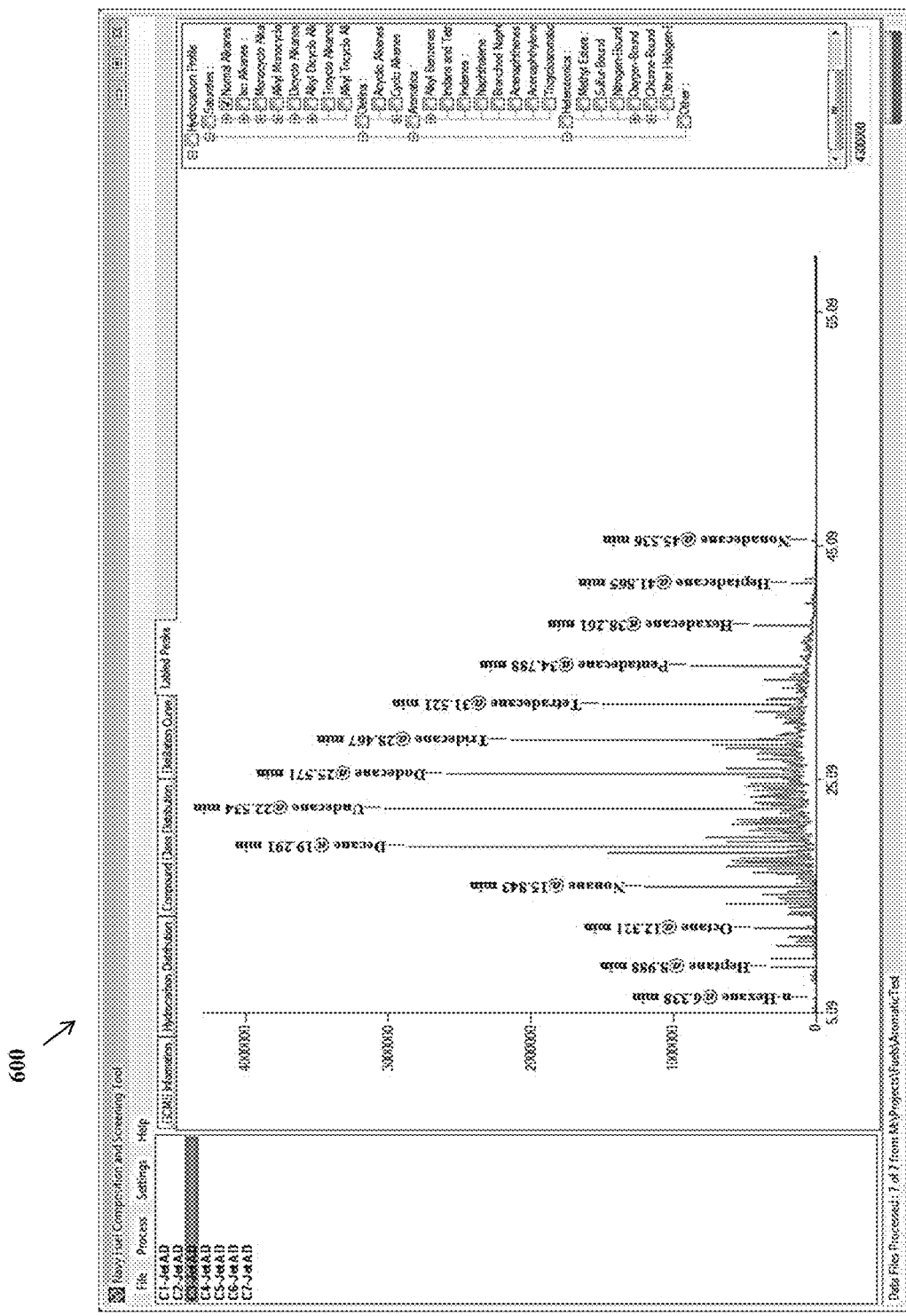
FIG. 6 is a software tool total ion chromatograph peak labeling option screen shot, showing alkane peak identities with GC retention times, in accordance with an exemplary embodiment of the invention.

As a general-purpose GC-MS interpretation and material classification tool, there can also be an option to produce a graphical image of the total ion chromatogram with user-selected peaks labeled with the compound identity. FIG. 6 is a software tool total ion chromatograph peak labeling option screen shot 600, showing alkane peak identities with GC retention times, in accordance with an exemplary embodiment of the invention. Each compound in the profiler output can have a check box next to every class and next to every compound detected. By selecting compound classes and/or specific compounds, the total ion chromatogram (TIC) shown in the "Labeled Peaks" window can display the names of the identified compounds above its peak in the TIC. The user can also select to display retention time and/or NIST library match factors.

This feature will thus graphically display where different classes of compounds or specific compounds appear in the chromatogram to provide the user with a snapshot of where these fuel constituents are eluting. This can aid method development and facilitate the generation of graphics for publication.

In summary, the purpose of this software tool is to provide a means to easily, reliably and accurately predict fuel performance properties using compositional information derived from analysis by gas chromatography-mass spectrometry (GC-MS). This can be accomplished with chemometric models that leverage the analytical capabilities of GC-MS data and correlate compositional information to fuel properties, and can be implemented in a software tool that operates on GC-MS instrument data files. This approach leads to fuel property prediction models that are not inherently constrained to the analysis of pre-defined fuel types.

Conventional fuel performance properties, specifications, and test methods are promulgated by the American Society of Testing and Materials (ASTM). The described invention predicts how a fuel will perform, as defined by a suite of ASTM fuel property measurements, enabling rapid fuel assessment in a single GC-MS data collection. This has applications in several aspects of fuel handling and use, covering both petrochemical and alternative fuels as appropriate, including point-of-use performance characterization; point-of-production performance characterization; prediction of overall suitability for Navy fuel certification procedures; short-term and long-term fuel stability prediction and monitoring; accelerated assessments through multiple simultaneous property predictions; lowering per-fuel analysis costs; investigation of blended fuel components and possible adulterants; and prediction of blending stocks necessary to attain desired performance characteristics.

The above examples are merely illustrative of several possible embodiments of various aspects of the present disclosure, wherein equivalent alterations and/or modifications will occur to others skilled in the art upon reading and understanding this specification and the annexed drawings. In particular regard to the various functions performed by the above described components (processor-executed processes, assemblies, devices, systems, circuits, and the like), the terms (including a reference to a "means") used to describe such components are intended to correspond, unless otherwise indicated, to any component, such as hardware, processor-executed software, or combinations thereof, which performs the specified function of the described component (i.e., that is functionally equivalent), even though not structurally equivalent to the disclosed structure which performs the function in the illustrated implementations of the disclosure. In addition, although a particular feature of the disclosure may have been illustrated and/or described with respect to only one of several implementations; such feature may be combined with one or more other features of the other implementations as may be desired and advantageous for any given or particular application. Also, to the extent that the terms "including", "includes", "having", "has", "with", or variants thereof are used in the detailed description and/or in the claims, such terms are intended to be inclusive in a manner similar to the term "comprising".

Portions of the invention can comprise a computer program that embodies the functions described herein. Furthermore, the modules described herein, such as the metaspectrum module, correlation module, blending module, and reporting module can be implemented in a computer system that comprises instructions stored in a machine-readable medium and a processor that executes the instructions. However, it should be apparent that there could be many different ways of implementing the invention in computer programming, and the invention should not be construed as limited to any one set of computer program instructions. Further, a skilled programmer would be able to write such a computer program to implement an exemplary embodiment based on the flow charts and associated description in the application text. Therefore, disclosure of a particular set of program code instructions is not considered necessary for an adequate understanding of how to make and use the invention. The inventive functionality of the claimed computer implemented tool is explained herein in more detail read in conjunction with the figures illustrating the program flow.

It should be understood that the foregoing relates only to illustrative embodiments of the present invention, and that numerous changes may be made therein without departing from the scope and spirit of the invention as defined by the following claims.

The invention claimed is:

1. A computer implemented method, comprising the steps of:
   identifying a plurality of compounds in data from an unknown fuel sample using a gas chromatography mass-spectrometry (GC-MS) technique;
   determining, based on the GC-MS technique, a plurality of chromatographic peaks corresponding to the plurality of compounds;
   identifying an abundance of every compound identified using the GC-MS technique, wherein the identifying comprises:
      determining respective identities for each chemical compound in the plurality of chemical compounds in the unknown fuel sample, and
      determining respective amounts of each chemical compound in the plurality of chemical compounds in the unknown fuel sample; and
   transforming, based on the identifying, the GC-MS data from the unknown fuel sample into a metaspectrum for the unknown fuel sample with a metaspectrum module, wherein the metaspectrum is a quantitative representation of the abundance of every compound identified using the GC-MS technique, wherein the metaspectrum module is implemented in a computer system that comprises instructions stored in a non-transitory machine-readable medium and a processor that executes the instructions;
   correlating, using a correlation module, the metaspectrum for the unknown fuel sample to a plurality of fuel properties of known fuel samples using a regression model, thereby generating a correlation, wherein the correlation module is implemented in a computer system that comprises instructions stored in a non-transitory machine-readable medium and a processor that executes the instructions; and
   determining a plurality of fuel property predictions for the unknown fuel sample based on the correlation, the determined identities for each compound in the plurality of compounds, and the determined amounts of each compound in the plurality of compounds.

2. The method of claim 1, wherein the step of transforming the GC-MS data from the unknown fuel sample into a single metaspectrum for the fuel sample comprises the steps of:
   locating all discernible chromatographic peaks in the GC-MS data set;
   identifying each peak against a mass spectral database; and
   calculating an area of each peak, which corresponds to the determined amounts of each compound in the plurality of compounds in the unknown fuel sample.

3. The method of claim 2, wherein the step of calculating an area of each peak further comprises determining a peak area threshold value that can be used to estimate match quality, wherein matches found for peaks below the peak area threshold value can be disregarded for the purposes of inclusion in the metaspectrum.

4. The method of claim 1, further comprising the step of mathematically blending GC-MS data from two fuels to predict the fuel properties and report the composition of a composite blend that comprises the two fuels.

5. A computer implemented system, comprising:
   a known fuels database comprising a plurality of data from gas chromatography-mass spectrometry analyses of a library of fuels with known fuel properties for a plurality of known fuel samples;
   gas chromatography-mass spectrometry (GC-MS) equipment configured to identify a plurality of compounds in data for an unknown fuel sample using a GC-MS technique;
   a metaspectrum module configured to:
      determine, based on the GC-MS technique, a plurality of chromatographic peaks corresponding to the plurality of compounds;
      identify an abundance of every compound identified using the GC-MS technique by:
         determining respective identities for each compound in the plurality of compounds in the unknown fuel sample, and
         determining respective amounts of each compound in the plurality of compounds in the unknown fuel sample based on respective areas of the plurality of chromatographic peaks, and
      transform, based on the identified abundance, the GC-MS data collected by the GC-MS equipment for the unknown fuel sample into a single metaspectrum for the unknown fuel sample, wherein the metaspectrum is a quantitative representation of the abundance of every compound identified using the GC-MS technique, and wherein the metaspectrum module is implemented in a computer system that comprises instructions stored in a non-transitory machine-readable medium and a processor that executes the instructions; and
   a correlation module configured to:
      correlate the metaspectrum for the unknown fuel sample to a plurality of fuel properties of known fuel samples using a regression model, thereby generating a correlation, wherein the correlation module is implemented in a computer system that comprises instructions stored in a non-transitory machine-readable medium and a processor that executes the instructions, and
      determine a plurality of fuel property predictions for the unknown fuel sample based on the correlation, the determined identities for each compound in the plurality of compounds, and the determined amounts of each compound in the plurality of compounds.

6. The system of claim 5, wherein the metaspectrum module is further configured to:
   locate all discernible chromatographic peaks in the GC-MS data set;
   identify each peak against a mass spectral database; and
   calculate an area of each peak, which corresponds to the determined amounts of each compound in the plurality of compounds in the unknown fuel sample.

7. The system of claim 5, further comprising a blending module configured to mathematically blend GC-MS data from two fuels to predict the fuel properties and report the composition of a composite blend that comprises the two fuels.

8. A method, comprising:
   receiving gas chromatography mass-spectrometry (GC-MS) data from an unknown fuel sample comprising a plurality of chemical compounds;

determining, based on the GC-MS data, a plurality of chromatographic peaks corresponding to the plurality of chemical compounds;

identifying an abundance of every compound identified using the GC-MS technique, wherein the identifying comprises:

determining respective identities for each chemical compound in the plurality of chemical compounds in the unknown fuel sample, and determining respective amounts of each chemical compound in the plurality of chemical compounds in the unknown fuel sample based on respective areas of the plurality of chromatographic peaks; and transforming, based on the identifying, the GC-MS data from the unknown fuel sample into a metaspectrum for the unknown fuel sample, wherein the metaspectrum is a quantitative representation of the abundance of every compound identified using the GC-MS technique; and determining a plurality of fuel property predictions for the unknown fuel sample based on the determined identities for each chemical compound in the plurality of chemical compounds and the determined amounts of each chemical compound in the plurality of chemical compounds.

9. The method of claim 8, wherein determining the respective identities for each chemical compound in the plurality of chemical compounds in the unknown fuel sample further comprises:

comparing each peak in the plurality of chromatographic peaks with information stored in a database of known fuel samples, wherein the database does not store information for the unknown fuel sample.

10. The method of claim 8, wherein respective areas of the plurality of chromatographic peaks correspond to respective abundances of chemical compounds in the unknown fuel sample.

11. The method of claim 8, further comprising:

estimating respective match qualities for the determined respective identities for each chemical compound based on respective peak area threshold values for each chemical compound.

12. The method of claim 8, wherein determining a plurality of fuel properties further comprises:

correlating, using the plurality of chromatographic peaks, metaspectra of library fuels to the plurality of fuel properties.

13. The method of claim 12, wherein correlating the metaspectra of library fuels to the plurality of fuel properties further comprises:

correlating the metaspectra of library fuels to the plurality of fuel properties using a partial least squares (PLS) regression.

14. The method of claim 8, wherein the plurality of fuel property predictions comprise a predicted density of the unknown fuel sample.

15. The method of claim 8, wherein the plurality of fuel property predictions comprise a predicted flash point of the unknown fuel sample.

16. The method of claim 8, wherein the plurality of fuel property predictions comprise a predicted viscosity of the unknown fuel sample.

17. The method of claim 8, wherein the plurality of fuel property predictions comprise a predicted pour point of the unknown fuel sample.

18. The method of claim 8, wherein the plurality of fuel property predictions comprise a predicted cloud point of the unknown fuel sample.

19. The method of claim 8, wherein the plurality of fuel property predictions comprise a predicted freeze point of the unknown fuel sample.

20. The method of claim 8, wherein the plurality of fuel property predictions comprise a predicted distillation characteristic of the unknown fuel sample.

* * * * *